(12) United States Patent
Fu et al.

(10) Patent No.: US 11,299,721 B2
(45) Date of Patent: Apr. 12, 2022

(54) ACID PHOSPHATASE MUTANT, USE THEREOF AND METHOD FOR PREPARING NICOTINAMIDE RIBOSIDE BY SAME

(71) Applicants: BONTAC BIO-ENGINEERING(SHENZHEN) CO., LTD, Guangdong (CN); Bontac InvitroLife Bio-technology(Shenzhen) Co., Ltd, Guangdong (CN); JIANGXI BONZYMES BIOTECHNOLOGY CO., LTD., Jiangxi (CN)

(72) Inventors: Rongzhao Fu, Guangdong (CN); Zhenwei Li, Guangdong (CN); Min Wang, Guangdong (CN); Xinglin Guo, Guangdong (CN)

(73) Assignees: Bontac Bio-Engineering (Shenzhen) Co., Ltd, Guangdong (CN); Bontac Invitrolife Bio-Technology (Shenzhen) Co., Ltd, Guangdong (CN); Jiangxi Bonzymes Biotechnology Co., Ltd., Jiangxi (CN)

(*) Notice: Subject to any disclaimer, the term of this patent is extended or adjusted under 35 U.S.C. 154(b) by 116 days.

(21) Appl. No.: 16/623,942

(22) PCT Filed: Aug. 17, 2018

(86) PCT No.: PCT/CN2018/101174
§ 371 (c)(1),
(2) Date: Dec. 18, 2019

(87) PCT Pub. No.: WO2019/210606
PCT Pub. Date: Nov. 7, 2019

(65) Prior Publication Data
US 2020/0224183 A1 Jul. 16, 2020

(51) Int. Cl.
*C12N 9/16* (2006.01)
*C12N 11/02* (2006.01)
*C12P 19/38* (2006.01)

(52) U.S. Cl.
CPC ............... *C12N 9/16* (2013.01); *C12N 11/02* (2013.01); *C12P 19/38* (2013.01); *C12Y 301/03002* (2013.01)

(58) Field of Classification Search
CPC combination set(s) only.
See application file for complete search history.

(56) References Cited

U.S. PATENT DOCUMENTS

2017/0121746 A1    5/2017   Velasquez et al.

FOREIGN PATENT DOCUMENTS

| CN | 1184157 A   | 6/1998  |
| CN | 101063126 A | 10/2007 |
| CN | 102382871 A | 3/2012  |
| CN | 103555687 A | 2/2014  |
| CN | 104342418 A | 2/2015  |

OTHER PUBLICATIONS

Singh RK et al. Protein Engineering Approaches in the Post-Genomic Era. Current Protein and Peptide Science. 2017. 18. 1-11. (Year: 2017).*
Zhang M et al. Propagated Perturbations from a Peripheral Mutation Show Interactions Supporting WW Domain Thermostability. Structure 2018. 26. 1474-1485. (Year: 2018).*
Dietrich, F.S., GenBank Accession nwnber NP_010954, Version NP_010954.I GenBank 04.4; 2018(Apr. 4, 2018); pp. 1-2.

* cited by examiner

*Primary Examiner* — Paul J Holland
(74) *Attorney, Agent, or Firm* — Muncy, Geissler, Olds & Lowe, P.C.

(57) ABSTRACT

An acid phosphatase mutant, and method for preparing nicotinamide riboside by same. The mutant is a protein of the following (a), (b) or (c): (a) a protein, having an amino acid sequence shown in SEQ ID NO: 3; (b) a protein, derived from (a), having catalytic activity higher than an acid phosphatase parent having an amino acid sequence shown in SEQ ID NO: 2, obtained by substituting, deleting or adding several amino acids in the amino acid sequence shown in SEQ ID NO: 3, using nicotinamide mononucleotide as a substrate; (c) a protein, having catalytic activity higher than the acid phosphatase shown in SEQ ID NO: 2, having 90% or more homology with the amino acid sequence of the protein defined by (a) or (b), and using nicotinamide mononucleotide as a substrate. It is used to prepare nicotinamide riboside and the conversion rate can be 99%.

5 Claims, 4 Drawing Sheets
Specification includes a Sequence Listing.

ACID PHOSPHATASE MUTANT, USE THEREOF AND METHOD FOR PREPARING NICOTINAMIDE RIBOSIDE BY SAME

CROSS REFERENCE TO RELATED APPLICATIONS

This application is a U.S. National Stage of International Application No. PCT/CN2018/101174 filed on Aug. 17, 2018, for which priority is claimed under 35 U.S.C. 120, the entire contents of which are incorporated herein by reference.

The instant application contains a Sequence Listing which has been submitted electronically in the ASCII text file and is hereby incorporated by reference in its entirety. The ASCII text file is a sequence listing entitled "2021-11-12-Sequence-Listing" created on Nov. 12, 2021 and having a size of 27,358 bytes in compliance of 37 CFR 1.821.

BACKGROUND

Technical Field

The present invention relates to the technical field of molecular biology and bioengineering, and in particular to an acid phosphatase mutant artificially obtained by a gene site-directed mutagenesis method, application thereof and a method for preparing nicotinamide riboside by the same.

Related Art

An acid phosphatase is a hydrolase, which can catalyze phosphate monoester (nucleotides, proteins, etc.) molecules and hydrolyze to remove phosphate groups, so that target molecules are dephosphorylated. The hydrolase is most effective in acidic environments, and thus called acid phosphatase, with the EC number of EC3.1.3.2.

Nicotinamide riboside (NR for short) is also known as nicotinamide nucleoside, nicotinamide ribonucleoside, nicotinic acid riboside/nucleoside, nicotinoyl nucleoside, and β-D-nicotinamide nucleoside, the CAS number is 1341-23-7, and its structural formula is shown in the following figure.

Nicotinamide riboside is a precursor of nicotinamide adenine dinucleotide (NAD) and represents a source of vitamin B3. Studies have shown that supplementation with nicotinamide riboside can increase the concentration of NAD in cells, thereby preventing and relieving various unhealthy conditions caused by NAD deficiency.

However, the nicotinamide riboside contains a high-energy glycosidic bond which is spontaneously unstable in an aqueous environment and decomposes into nicotinamide and ribose products. This spontaneous decomposition occurs in a few hours or a few days according to specific environmental conditions, so that it is difficult to maintain any naturally existing nicotinamide riboside in food, and it is also difficult to obtain nicotinamide riboside obtained by separating from natural sources, so the nicotinamide riboside is generally produced by a chemical synthesis method currently at home and abroad.

A method for producing nicotinamide riboside is disclosed in U.S. Patent Application Ser. No. US/01/0121746 A1. The nicotinamide riboside is produced by catalyzing nicotinamide mononucleotide and/or a derivative thereof, water and a specific solvent as raw materials by a phosphate monoester hydrolase. By adopting an enzymatic method for preparing the nicotinamide riboside, the method has the advantages of being more environmentally friendly and healthier and more simple in process than the chemical synthesis method, and is a development trend of nicotinamide riboside production. However, the activity of wild-type acid phosphatase is relatively low, which leads to higher cost of production of nicotinamide riboside by the enzymatic method. Therefore, an improvement in enzyme activity of acid phosphatase is of great significance for promoting the industrial production of nicotinamide riboside by the enzymatic method.

SUMMARY

The present invention is directed to an acid phosphatase with improved enzyme activity and a method for preparing nicotinamide riboside by applying the same in order to solve the technical problem that the cost of industrial production of nicotinamide riboside by an enzymatic method is relatively high due to the relatively low activity of a wild type acid phosphatase.

To achieve the above objective, the present invention first provides an acid phosphatase mutant, which is a protein of the following (a), (b) or (c):

(a) a protein, having an amino acid sequence shown in SEQ ID NO: 3;

(b) a protein, derived from (a), having catalytic activity higher than an acid phosphatase parent having an amino acid sequence shown in SEQ ID NO: 2, obtained by substituting, deleting or adding one or several amino acids in the amino acid sequence shown in SEQ ID NO: 3, and using nicotinamide mononucleotide as a substrate; and (c) a protein, having catalytic activity higher than the acid phosphatase parent shown in SEQ ID NO: 2, having 90% or more homology with the amino acid sequence of the protein defined by (a) or (b), and using nicotinamide mononucleotide as a substrate.

The above-mentioned acid phosphatase parent is derived from Saccharomyces cerevisiae, a gene sequence thereof is shown in SEQ ID NO: 1, and an amino acid sequence is shown in SEQ ID NO: 2.

Preferably, compared with the amino acid sequence of the acid phosphatase parent as shown in SEQ ID NO: 2, the mutant of the present invention has at least one mutation at at least one of the following sites: $44^{th}$ site, $115^{th}$ site, $206^{th}$ site and $240^{th}$ site.

More preferably, compared with the amino acid sequence of the acid phosphatase parent as shown in SEQ ID NO: 2, the mutant of the present invention has at least one of the following mutations: K44C, K115F, K115I, D206I and S240E.

The present invention also provides a method for preparing nicotinamide riboside, including: catalyzing nicotinamide mononucleotide by acid phosphatase to convert into nicotinamide riboside in the presence of KCl and anhydrous MgCl$_2$, where the acid phosphatase is an acid phosphatase parent having an amino acid sequence shown in SEQ ID NO: 2 or an acid phosphatase mutant of the following (a), (b) or (c):

(a) a protein, having an amino acid sequence shown in SEQ ID NO: 3;

(b) a protein, derived from (a), having catalytic activity higher than an acid phosphatase parent having an amino acid sequence shown in SEQ ID NO: 2, obtained by substituting, deleting or adding one or several amino acids in the amino acid sequence shown in SEQ ID NO: 3, and using nicotinamide mononucleotide as a substrate; and (c) a protein, having catalytic activity higher than the acid phosphatase parent shown in SEQ ID NO: 2, having 90% or more homology with the amino acid sequence of the protein defined by (a) or (b), and using nicotinamide mononucleotide as a substrate.

A conversion route of the method for preparing the nicotinamide riboside of the present invention is shown in the following figure.

Preferably, the method for preparing the nicotinamide riboside of the present invention sequentially includes the following steps: 1) dissolving KCl and anhydrous MgCl$_2$ in water to obtain a mixed solution of KCl and MgCl$_2$; 2) cooling to room temperature; 3) adding the nicotinamide mononucleotide to the mixed solution of KCl and MgCl$_2$, dissolving and adjusting a pH value to 6 to 7; 4) adding the acid phosphatase and adjusting the pH value to 6.8 to 7.3; and 5) reacting at a temperature of 37±5° C. for at least 1.5 hours.

In order to prevent the substrate nicotinamide mononucleotide from being degraded, more preferably, konjac glucomannan and/or rebaudioside A are/is added to a reaction system before an enzyme reaction that the acid phosphatase catalyzes the nicotinamide mononucleotide to convert into the nicotinamide riboside starts. More preferably, konjac glucomannan is added.

More preferably, the konjac glucomannan and/or rebaudioside A are/is added in an amount of 0.1 to 0.5 time the weight of the nicotinamide mononucleotide.

The method of the present invention includes the steps of first dissolving KCl and anhydrous MgCl$_2$ and then adding the substrate nicotinamide mononucleotide after cooling to room temperature. The method has the advantages of avoiding the effect of excessive heat generated during the dissolution process on the substrate, thereby preventing a reduction in a conversion rate.

Preferably, water in step 1) of the method of the present invention is selected from double distilled water to avoid the effect of impurities in the water on the substrate, thereby preventing the reduction in the conversion rate. The so-called double distilled water refers to water obtained by re-distilling single distilled water. The English name is double distilled water, ddwater for short, and also written as ddH$_2$O.

Preferably, the pH value is adjusted using NaOH in steps 3) and 4) of the method of the present invention.

Preferably, the final concentration of the nicotinamide mononucleotide in the reaction system is 100±50 g/L in the method of the present invention.

Preferably, the final concentration of KCl in the reaction system is 15±5 g/L in the method of the present invention.

Preferably, the final concentration of MgCl$_2$ in the reaction system is 40±10 g/L in the method of the present invention.

In the method of the present invention, the acid phosphatase parent is derived from Saccharomyces cerevisiae, the gene sequence thereof is shown in SEQ ID NO: 1, and the amino acid sequence is shown in SEQ ID NO: 2.

The acid phosphatase used in the method of the present invention may be a commercial enzyme purchased from the market, or may be a self-prepared enzyme product, and the enzyme product herein may be in a form of unpurified crude enzyme, or may be a completely or partially purified enzyme. The acid phosphatase of the present invention can be self-prepared by the following method:

preparation of an acid phosphatase parent: the gene sequence shown in SEQ ID NO: 1 is amplified by a PCR technology; then an amplified product is inserted into NdeI and EcoR I sites of an expression vector pET22b(+) to obtain a recombinant plasmid pET22b-NS3; after being validated by sequencing, the recombinant plasmid pET22b-NS3 is transferred into *E. coli* and cultured and induced to express; and after the expression is completed, a thallus is collected for cell disruption, and then a supernatant is collected to obtain a crude enzyme solution of the acid phosphatase parent.

Preparation of an acid phosphatase mutant: primer sequences of mutation sites are designed by a reverse PCR technology; reverse PCR amplification is performed using the designed primers and the recombinant plasmid pET22b-NS3 as a template; then the amplified product is treated with a Dpn I enzyme digestion template and then transformed into *E. coli*; the transformed *E. coli* is cultured and induced to express; after the expression is completed, a thallus is collected for cell disruption, and then a supernatant is collected to obtain a crude enzyme solution of the acid phosphatase mutant.

Preferably, the acid phosphatase used in the method of the present invention is a pure enzyme solution obtained by subjecting the crude enzyme solution of the above-mentioned acid phosphatase parent and/or mutant to a purification treatment.

Preferably, the crude enzyme solution of the above-mentioned acid phosphatase parent and/or mutant is subjected to the purification treatment by a nickel column.

Preferably, a method for subjecting the crude enzyme solution of the above-mentioned acid phosphatase parent and/or mutant to the purification treatment by the nickel column includes: 1) preparation of the nickel column: taking agarose gel as a nickel carrier, hanging nickel with a nickel chloride solution, and equilibrating the nickel column with a 1×PBS+10 mM imidazole solution; 2) loading: uniformly mixing the crude enzyme solution with a nickel filler and incubating in an ice bath for 1 to 2 h; and then loading the incubated mixture to the nickel column prepared in step 1); 3) elution: firstly eluting with the 1×PBS+10 mM imidazole solution for the first time; then eluting with a 1×PBS+(200 to 500) mM imidazole solution for the second time, and collecting an eluent to obtain the pure enzyme solution.

Of course, the above-mentioned purification treatment method using the nickel column is also suitable for purifying crude enzyme solutions of other acid phosphatases other than the acid phosphatase parent and mutant of the present invention.

In the above-mentioned method for subjecting the crude enzyme solution to the purification treatment, the first-time elution aims to remove a heteroprotein, and the second-time elution aims to elute an acid phosphatase protein.

Preferably, the acid phosphatase in the method of the present invention is selected from an immobilized enzyme. The so-called immobilized enzyme refers to an enzyme that plays a catalysis role in a certain spatial range and can be used repeatedly and continuously. Usually, the enzyme catalysis reaction is carried out in an aqueous solution, and the immobilized enzyme is in a state in which a water-soluble enzyme is treated physically or chemically to make it insoluble in water but still has an enzyme activity. After the enzyme is immobilized, the stability is generally increased, the enzyme is easy to separate from the reaction system, is easy to control, can be repeatedly used for many times, is convenient for transportation and storage, and is advantageous for automated production.

The immobilized enzyme used in the method of the present invention can be directly purchased from the market, or can be self-prepared, or can be self-immobilized after a non-immobilized enzyme is purchased. In the immobilization, various enzyme immobilization carriers known in the art may be used, such as a conventional inorganic carrier material silica, activated carbon, and glass beads, and such as an organic polymer carrier macroporous poly N-aminoethyl acrylamide-polyethylene. In the present invention, the acid phosphatase is immobilized using a nickel material or a solid phase resin preferably.

Preferably, a method for immobilizing the acid phosphatase with the solid phase resin includes: adding 0.2 to 0.8 M $K_2HPO_4$ to the acid phosphatase, adjusting the pH value to 7.5 to 9.5, adding the solid phase resin to stir at room temperature for 12 to 24 h, and then filtering to remove a filtrate to obtain an acid phosphatase immobilized enzyme.

Of course, the above-mentioned immobilization method is equally applicable to the immobilization of other acid phosphatases other than the acid phosphatase parent and mutant of the present invention.

Preferably, the method for preparing the nicotinamide riboside provided by the present invention also includes a post-treatment process for obtaining a nicotinamide riboside refined product by purifying an enzyme reaction solution in which the nicotinamide mononucleotide is catalyzed by the acid phosphatase to convert into the nicotinamide riboside, including the following steps: 1) filtering the enzyme reaction solution to collect a filtrate; 2) adjusting the pH value of the filtrate to 5.0±0.5 to improve the stability of the nicotinamide riboside in the solution; 3) microfiltering the filtrate of which the pH value is adjusted in step 2) to collect a filtrate; 4) purifying a microfiltrate obtained by microfiltering in step 3) with a preparative liquid phase, the preparative liquid phase using polystyrene as a filler of a preparation column, using ethanol and water as a mobile phase, performing gradient elution, and collecting an eluate of a peak of interest; and 5) lyophilizing the eluate collected in step 4) to obtain the nicotinamide riboside refined product.

The filtration in the method of the present invention refers to a process of separating a solid and a liquid in a solution by a physical method. The common filtering methods are all applicable to the present invention, including atmospheric filtration, vacuum filtration, centrifugal filtration, and the like. Preferably, in step 1) of the above-mentioned post-treatment process, the enzyme reaction solution is filtered using a 200-400 mesh filter membrane to remove the acid phosphatase in the enzyme reaction solution.

Microfiltration, also known as millipore filtration, uses a microfiltration membrane as a filter medium, retains particles and bacteria between 0.1 and 1 micron under the driving of pressure of 0.1 to 0.3 MPa, but allows macromolecular organics and inorganic salts to pass. Preferably, the filtrate is subjected to microfiltration using a 0.45 μm microfiltration membrane in step 3) of the above-mentioned post-treatment process.

Preferably, in step 4) of the above-mentioned post-treatment process, the flow rate of the mobile phase is 40 ml/min, the detection wavelength is 260 nm, and the elution gradient is as follows: 0 to 13 min, 0% of ethanol, and 100% of water; 13 to 23 min, 1% of ethanol, and 99% of water; 23 to 31 min, 5% of ethanol, and 95% of water; 31 to 43 min, 20% of ethanol, and 80% of water; 43 to 45 min, 20% of ethanol, and 80% of water; and 45 to 60 min, 100% of ethanol, and 0% of water.

Preferably, prior to lyophilization in step 5) of the above-mentioned post-treatment process, the pH value of the collected eluate is adjusted to 3 to 4 with hydrochloric acid, and under the pH condition, the nicotinamide riboside is all reacted with hydrochloric acid to generate nicotinamide riboside chloride.

In order to obtain the nicotinamide riboside having higher stability and better properties, preferably, konjac glucomannan and/or rebaudioside A are/is added to the collected eluate and mixed uniformly prior to lyophilization in step 5) of the above-mentioned post-treatment process.

More preferably, the konjac glucomannan and/or rebaudioside A are/is added in an amount of 1 to 2 times the weight of the nicotinamide riboside, further preferably 1.5 times the weight of the nicotinamide riboside.

In order to improve the efficiency of lyophilization and shorten the time of lyophilization, preferably, the collected eluate is subjected to a concentration treatment to remove a large amount of moisture prior to lyophilization in step 5) of the above-mentioned post-treatment process. The concentration in the present invention refers to a process of evaporating a solvent by adopting a physical method to increase the concentration of the solution, including a vacuum distillation method, an ultrafiltration method, a dialysis method, an adsorption method, a lyophilization method, and the like.

Preferably, the eluent is concentrated until the concentration of nicotinamide riboside is 40 to 90 g/L.

In order to prevent the nicotinamide riboside from being degraded, preferably, the concentration treatment process is controlled to be carried out at a temperature of 25° C. or below; and more preferably, the concentration treatment process is controlled to be carried out at a temperature of 20° C. or below.

More preferably, the above concentration treatment adopts nanofiltration concentration.

Nanofiltration is a pressure-driven membrane separation process between reverse osmosis and ultrafiltration. A nanofiltration membrane is used as a filter medium, is in the range of a few nanometers in pore diameter, and allows solvent molecules or some solutes with smaller relative molecular mass or low-valence ions to penetrate, so as to achieve the effects of separation and concentration.

Preferably, the sublimation temperature in the lyophilization process in step 5) of the above-mentioned post-treatment process is controlled at 25° C. or below. Preferably, the lyophilization is performed until the moisture content in the nicotinamide riboside refined product is 2% or below.

The present invention also provides a method for preparing an acid phosphatase immobilized enzyme, including:

1) preparation of an acid phosphatase parent, including: amplifying a gene sequence of the acid phosphatase parent by a PCR technology; then inserting an amplified product into an expression vector to obtain a recombinant plasmid; after validation by sequencing, transforming the recombinant plasmid into host cells and performing culturing and inducible expression; after the expression is completed, collecting cells and performing a cell disruption treatment, and then collecting a supernatant to obtain a crude enzyme solution of the acid phosphatase parent;

2) preparation of an acid phosphatase mutant, including: designing primer sequences of mutation sites by utilizing an inverse PCR technology; utilizing the designed primers to perform reverse PCR amplification using the recombinant plasmid in step 1) as a template; then treating the amplified product with a Dpn I enzyme digestion template and then transforming into host cells, and performing culturing and inducible expression; and after the expression is completed, collecting cells and performing a cell disruption treatment, and then collecting a supernatant to obtain a crude enzyme solution of the acid phosphatase mutant;

3) purification of the crude enzyme solution of the acid phosphatase parent and/or mutant using a nickel column, including: a) preparation of the nickel column: using agarose gel as a nickel carrier, hanging nickel with a nickel chloride solution, and using a 1×PBS+10 mM imidazole solution to equilibrate the nickel column; b) loading: uniformly mixing the crude enzyme solution of the acid phosphatase parent and/or mutant with a nickel filler and then incubating in an ice bath for 1 to 2 h; then loading the incubated mixture to the nickel column prepared in step a); and c) elution: firstly eluting with a 1×PBS+10 mM imidazole solution for the first time; then eluting with a 1×PBS+(200 to 500) mM imidazole solution for the second time, and collecting an eluate to obtain a pure enzyme solution of the acid phosphatase parent and/or mutant; and 4) immobilization using a solid phase resin, including: adding 0.2 to 0.8 M $K_2HPO_4$ to the purified enzyme solution obtained in step 3), adjusting the pH value to 7.5 to 9.5, and then adding the solid phase resin to stir at room temperature for 12 to 24 h, and filtering to remove a filtrate to obtain an acid phosphatase immobilized enzyme.

In the above-mentioned method for preparing the acid phosphatase immobilized enzyme, the acid phosphatase is the above-mentioned acid phosphatase parent and mutant of the present invention, and may also be other acid phosphatase parents and mutants other than the acid phosphatase parent and mutant of the present invention.

The present invention also provides a biological material, including a recombinant vector, a recombinant cell or a recombinant microorganism. The biological material includes a gene encoding the above-mentioned acid phosphatase mutant of the present invention.

The present invention also provides application of the above-mentioned acid phosphatase mutant in preparation of nicotinamide riboside.

Beneficial Effects:

Compared with the acid phosphatase parent, the acid phosphatase mutant provided by the present invention is more obviously improved in enzyme activity, temperature stability and pH stability. According to the method for preparing the nicotinamide riboside provided by the present invention, the conversion rate of the substrate nicotinamide mononucleotide can be as high as 99%, and the purity of the prepared nicotinamide riboside can reach 99% or more.

DETAILED DESCRIPTION

The present invention will be further described in detail below with reference to the specific embodiments and the accompanying drawings. The following embodiments illustrate the present invention. The present invention is not limited to the following embodiments, and the embodiments in which specific conditions are not specified are implemented according to conventional conditions or conditions recommended by manufacturers. Unless otherwise stated, the raw materials and other chemical reagents used in the embodiments of the present invention are commercially available goods.

Embodiment 1

Preparation of Acid Phosphatase Parent.

Figure 1:
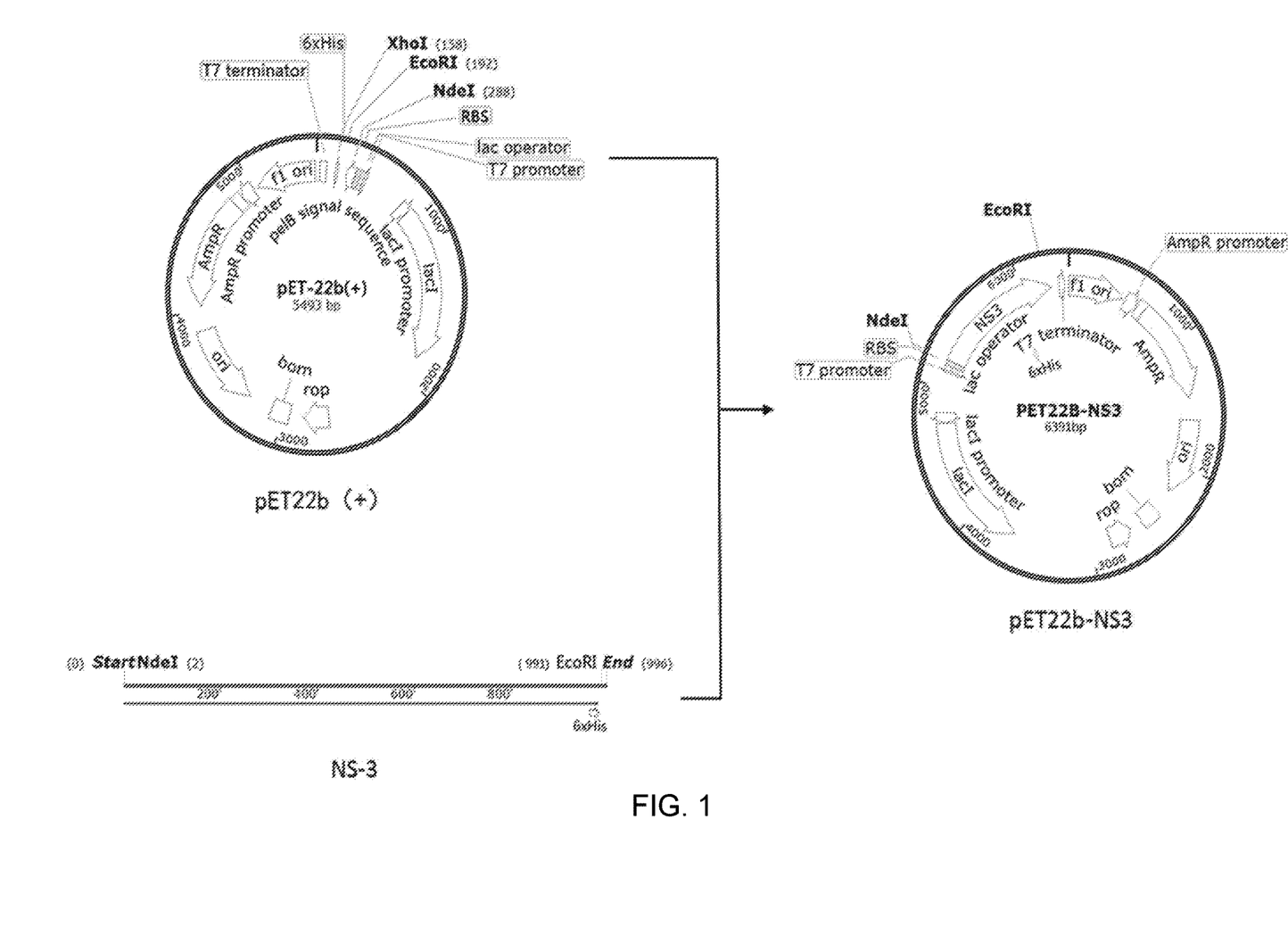
FIG. 1 is a construction process diagram of a recombinant plasmid pET22b-NS3 in Embodiment 1 of the present invention.

An acid phosphatase gene NS-3 (the amino acid sequence thereof is shown in SEQ ID NO: 2) shown in SEQ ID NO: 1 and derived from Saccharomyces cerevisiae was amplified by a PCR amplification technology using the following primer pair 5'-GGAATTCCATATGATGACCAT-TGCGAAGGATTACCGT-3' and 5'-CCGGAATT CTTAGTGGTGGTGGTGGTGGT-3', an obtained PCR amplification product was digested and simultaneously inserted into NdeI and EcoR I sites of an expression vector pET22b(+) to obtain a recombinant plasmid pET22b-NS3, as shown in FIG. 1. After being validated by sequencing, the recombinant plasmid was transferred into E. coli Rosetta (de3). The obtained recombinant E. coli was inoculated into a small volume of LB medium (containing 100 μg/mL of Amp), cultured at a temperature of 30 to 37° C. overnight, and then transferred to a certain volume of LB medium (containing 100 µg/mL of Amp) at an inoculated dose of 1 to 5%, continuously cultured at a temperature of 30 to 37° C. until OD600 reaches 0.6 to 1.0, added with isopropyl-β-D-thiogalactoside (IPTG) having a final concentration of 0.1 mM to 1 mM, and induced to express at a temperature of 20 to 37° C. for 10 to 20 hours, and then a thallus was collected by centrifugation.

Embodiment 2

Preparation of Acid Phosphatase Mutant The following mutation sites: K44C (SEQ ID NO: 7), K115F (SEQ ID NO: 5), K115I (SEQ ID NO: 3), D206I (SEQ ID NO: 4), S240E (SEQ ID NO: 6), K115I/S240E (SEQ ID NO: a), K115F/K44C/D206I (SEQ ID NO: 9), and K115I/S240E/D206I (SEQ ID NO: 10) were designed, mutant primer sequences shown in Table 1 were utilized to perform reverse PCR by using the recombinant plasmid pET22b-NS3 constructed in Embodiment 1as a template. The PCR system and PCR procedure were as follows:

PCR system:

| PrimeSTAR ® GXL DNA Polymerase | 0.5 ul |
| 5×PrimeSTAR GXL Buffer (Mg2+ plus)*2 | 0 ul |
| Template plasmid | 1 ul |
| dNTP (2.5 mM each) | 4 ul |
| Mutant primer 1 | 1 ul |
| Mutant primer 2 | ul |
| Sterile water | up to 50 ul |

PCR procedure:

| 98° C. | 3 min |
| 98° C. 10 s | |
| 30 × 50-65° C. 15 s | |
| 72° C. | 7 min |
| Cycle 30 times | |
| 72° C. | 10 min |

A PCR product was purified by a gel extraction kit, and then digested with DpnI. After digestion, the product was transferred into *E. coli* DH5a. After screening by an Amp plate, colonies were picked and sent for sequencing. It was confirmed that the mutant recombinant plasmid with successful mutation at K44C, K115F, K115I, D206I. S240E, K115I/S240E, K115F/K44C/D206I, and K115I/S240E/D206I sites was transferred into *E. coli* Rosetta (de3). The obtained mutant recombinant *E. coli* was inoculated into a small volume of LB medium (containing 100 µg/mL of Amp), cultured at a temperature of 30 to 37° C. overnight, and then transferred to a certain volume of LB medium (containing 100 µg/mL of Amp) at an inoculated dose of 1 to 5%, continuously cultured at a temperature of 30 to 37° C. until OD600 reaches 0.6 to 1.0, added with isopropyl-β-D-thiogalactoside (IPTG) having a final concentration of 0.1 mM to 1 mM, and induced to express at a temperature of 20 to 37° C. for 10 to 20 h, and then a thallus was collected by centrifugation.

TABLE 1

| Primer name | Primer sequence (5' to 3') |
|---|---|
| D206I_F | 5'-TTCATCTGCAAGCCGATTCCGAAATTTTTCGAG-3' |
| D206I_R | 5'-CTCGAAAAATTTCGGAATCGGCTTGCAGATGAA-3' |
| K115I_F | 5'-GGCCTGATTAAGAACATTCAGATCGATGACGTT-3' |
| K115I_R | 5'-AACGTCATCGATCTGAATGTTCTTAATCAGGCC-3' |
| K115F_F | 5'-GGCCTGATTAAGAACTTCCAGATCGATGACGTT-3' |
| K115F_R | 5'-AACGTCATCGATCTGGAAGTTCTTAATCAGGCC-3' |
| S240E_F | 5'-GTGCGTAGCGCGCTGGAAATGGGTATGGGCCAC-3' |
| S240E_R | 5'-GTGGCCCATACCCATTTCCAGCGCGCTACGCAC-3' |
| K44C_F | 5'-GAAGTGGACCCGCCGTGCCTGCCGGATCCGGAC-3' |
| K44C_R | 5'-GTCCGGATCCGGCAGGCACGGCGGGTCCACTTC-3' |

Embodiment 3

Preparation of Crude Enzyme Solution of Acid Phosphatase

A thallus collected was resuspended and fermented using a 1×PBS+10 mM imidazole solution of which the mass is 4 times the mass of the thallus, and then the thallus was disrupted by a high-pressure homogenizer; after the homogenization was completed, 0.5 to 1% of the total volume of polyethyleneimine (PEI) was added under stirring, and the pH was adjusted to 7.0 to 8.0; and a supernatant clarified enzyme solution was collected by centrifugation, the enzyme solution was filtered through a 0.45 µL filter membrane, and a filtrate was collected to obtain a crude enzyme solution of acid phosphatase.

Embodiment 4

Preparation of Nickel Column a) after a column was cleaned, agarose gel was used as a nickel carrier, the agarose gel was taken according to a ratio of nickel filler (ml) to thallus (g) of 1 to 2, and the agarose gel was washed by successively using ddH2O and 1×PBS with 5 column volumes separately;

b) after a 0.2 mol/L nickel chloride solution was prepared, nickel was hung, and in order to fully hang the nickel, the hanging may be repeated; and c) unbound $Ni^{2+}$ was washed away with 5 column volumes of $ddH_2O$, and the nickel column was equilibrated with 5 to 10 column volumes of a 1×PBS+10 mM imidazole solution (pH=8.0).

Embodiment 5

Loading and Elution a) The crude enzyme solution of the acid phosphatase obtained in Embodiment 3 was uniformly mixed with the nickel filler, then transferred to a conical flask, and incubated in a ice bath on a shaker for 1 to 2 h at a rotation speed of 100 rm;

b) a heteroprotein was eluted with a 1×PBS+10 mM imidazole solution (pH=8.0), and a target protein was fully eluted with a 1×PBS+200 mM imidazole solution (pH=8.0), and an eluate was collected to obtain a pure enzyme solution of acid phosphatase.

Embodiment 6

Enzyme Activity Comparison Experiment

Determination method of enzyme activity: KCl having a final concentration of 200 mM and $MgCl_2$ having a final concentration of 400 mM were used as cofactors, NMN having a final concentration of 2 mmol was added to a 200 uL reaction system, then 10 uL of the diluted pure enzyme solution was added, and the pure enzyme solution was replaced with a corresponding buffer in a blank control; the solutions were uniformly mixed to react for 10 min under the conditions that the temperature was 37° C. and the pH was 7.0, then 200 μL of a 10% trichloroacetic acid solution was immediately added to be uniformly mixed, the reaction was terminated, a sample was taken and diluted with methanol by 50 times, then the amount of the product was determined by HPLC, and the enzyme activity unit U was calculated.

Definition of enzyme activity U of acid phosphatase: the amount of enzyme required to hydrolyze the substrate NMN in 1 minute to release 1 umol under the conditions that the temperature is 37° C. and the pH is 7.0 is called one enzyme activity international unit (U).

The comparison experiment results of the enzyme activity and stability of the acid phosphatase parent and the acid phosphatase mutant of the present invention are shown in Table 2, where the temperature stability and pH stability mean that the target enzyme is in a storage range that after the target enzyme is stored for 12 h under the corresponding storage conditions, the residual activity is more than or equal to 90%.

TABLE 2

| Type | Enzyme activity U | Temperature stability | pH stability |
|---|---|---|---|
| Parent | 365.8 ± 8.5 | 4-35° C. | 6.0-8.0 |
| D206I | 413.7 ± 5.3 | 4-35° C. | 6.0-8.0 |
| K115I | 826.8 ± 6.3 | 4-50° C. | 5.0-9.0 |
| K115F | 441.5 ± 9.6 | 4-40° C. | 6.0-8.5 |
| S240E | 502.9 ± 4.8 | 4-35° C. | 5.5-8.0 |
| K44C | 392.6 ± 7.4 | 4-35° C. | 6.0-8.0 |
| K115I/S240E | 931.7 ± 3.1 | 4-50° C. | 4.5-9.0 |
| K115F/K44C/D206I | 964.5 ± 5.2 | 4-50° C. | 5.0-9.0 |
| K115I/S240E/D206I | 1038.8 ± 6.7 | 4-55° C. | 5.0-9.5 |

The results show that compared with the acid phosphatase parent, the acid phosphatase mutant of the present invention is more obviously improved in enzyme activity, temperature stability and pH stability.

Embodiment 7

Preparation of Nicotinamide Riboside

Figure 2:
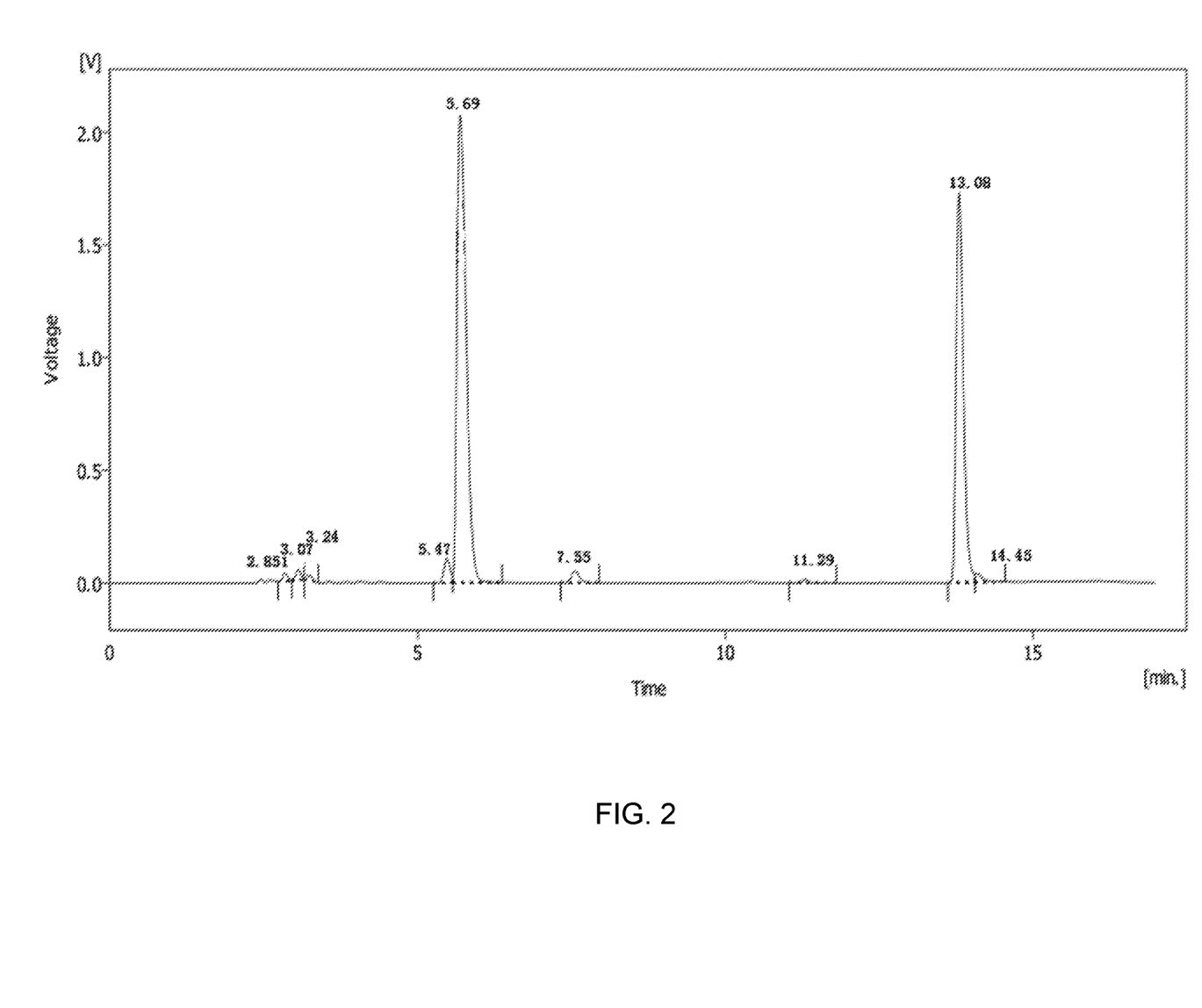
FIG. 2 is an HPLC chromatogram of an enzyme reaction solution of a mutant K115I in Embodiment 7.

A 2 L total system was designed, the final concentration of a substrate was set to 100 g/L, a clean 3 L three-necked bottle was prepared, 1 L of ddH₂O was added, then 30 g of KCl and 80 g of anhydrous $MgCl_2$ were added to be stirred and dissolved, after the solution temperature drops to room temperature, 200 g of NMN was added, and the pH was adjusted to 6 to 7 with 5 M NaOH so that the dissolution was complete. The reaction temperature was set to 37° C., 900 ml of the pure enzyme solution of the acid phosphatase mutant K115I obtained in Embodiment 5 was added, and a sodium phosphate buffer of pH 7.0 was used to be supplemented to the 2 L system, and the reaction system was adjusted to pH 7.2 to start reaction. After reacting for 2 hours, a reaction solution was taken and diluted by 50 to 100 times with pure water, and the results of the reaction were analyzed by high performance liquid chromatography after millipore filtration. The analysis method is shown in Table 3, and the HPLC chromatogram is shown in FIG. 2. The detection results show that the substrate NMN is degraded more obviously, about 42% of the substrate is degraded, and the conversion rate of the remaining NMN to NR is 99.9%.

TABLE 3

| | | | |
|---|---|---|---|
| Chromatographic column | Welch Xtimate C18 5 μm × 250 × 4.6 mm | | |
| Mobile phase A: | Sodium dihydrogen phosphate buffer (a 100 mM aqueous solution of sodium dihydrogen phosphate, pH adjusted to 6.6 with 6 mol of sodium hydroxide) | | |
| Mobile phase B: | Methanol (chromatographic grade) | | |
| Instrument model | Thermo Fisher U3000 | | |
| Detector | UV260 nm | | |
| Flow rate: | 1.0 ml/min | | |
| Column temperature: | 25° C. | | |
| Injection volume: | 20 μl | | |
| Sample treatment | Dissolve in water | | |
| Gradient: | Time/min | Phase A(%) | Phase B(%) |
| | 0 | 99 | 1 |
| | 4 | 99 | 1 |
| | 5 | 95 | 5 |
| | 10 | 85 | 15 |
| | 12 | 80 | 20 |
| | 12.1 | 99 | 1 |
| | 16 | 99 | 1 |
| Remarks: | Calculated by volume ratio | | |

Embodiment 8

Figure 3:
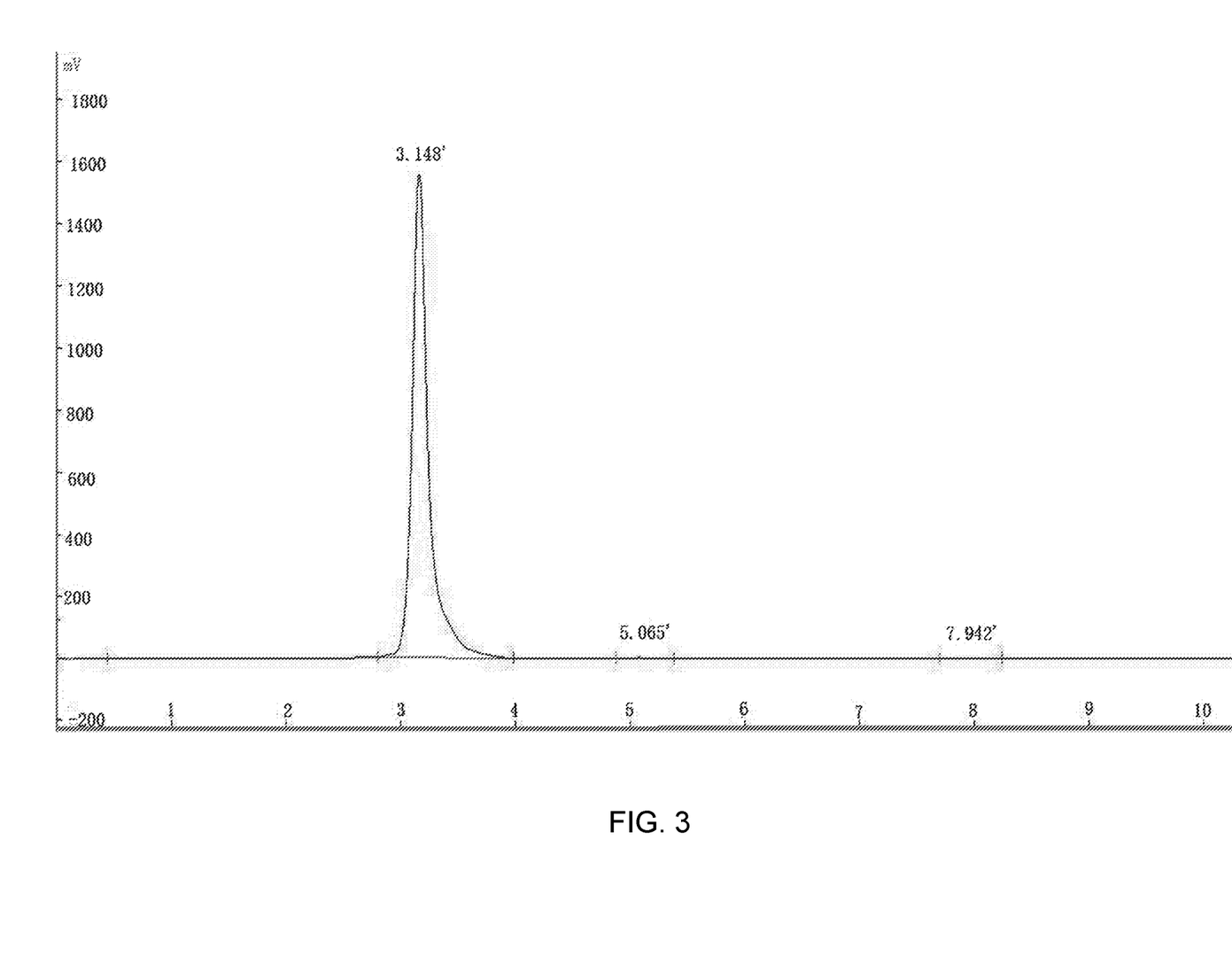
FIG. 3 is an HPLC chromatogram of an enzyme reaction solution of a parent in Embodiment 8.

A 2 L total system was designed, the final concentration of the substrate was set to 100 g/L, a clean 3 L three-necked bottle was prepared, 1 L of ddH₂O was added, then 30 g of KCl and 80 g of anhydrous $MgCl_2$ were added to be stirred and dissolved, after the solution temperature drops to room temperature, 20 g of konjac glucomannan was added, then 200 g of NMN was added and the pH was adjusted to 6 to 7 with 5 M NaOH so that the dissolution was complete. The reaction temperature was set to 37° C., 900 ml of the pure enzyme solution of the acid phosphatase mutant K115I obtained in Embodiment 5 was added, and a sodium phosphate buffer of pH 7.0 was used to be supplemented to the 2 system, and the reaction system was adjusted to pH 7.2 to start reaction. After reacting for 2 hours, a reaction solution was taken and diluted by 50 to 100 times with pure water, and the results of the reaction were analyzed by high performance liquid chromatography after millipore filtration. The analysis method is shown in Table 3, and the HPLC chromatogram is shown in FIG. 3. The detection results show that the substrate NMN is not degraded obviously, and the conversion rate of NMN to NR is 99.8%.

Embodiment 9

Figure 4:
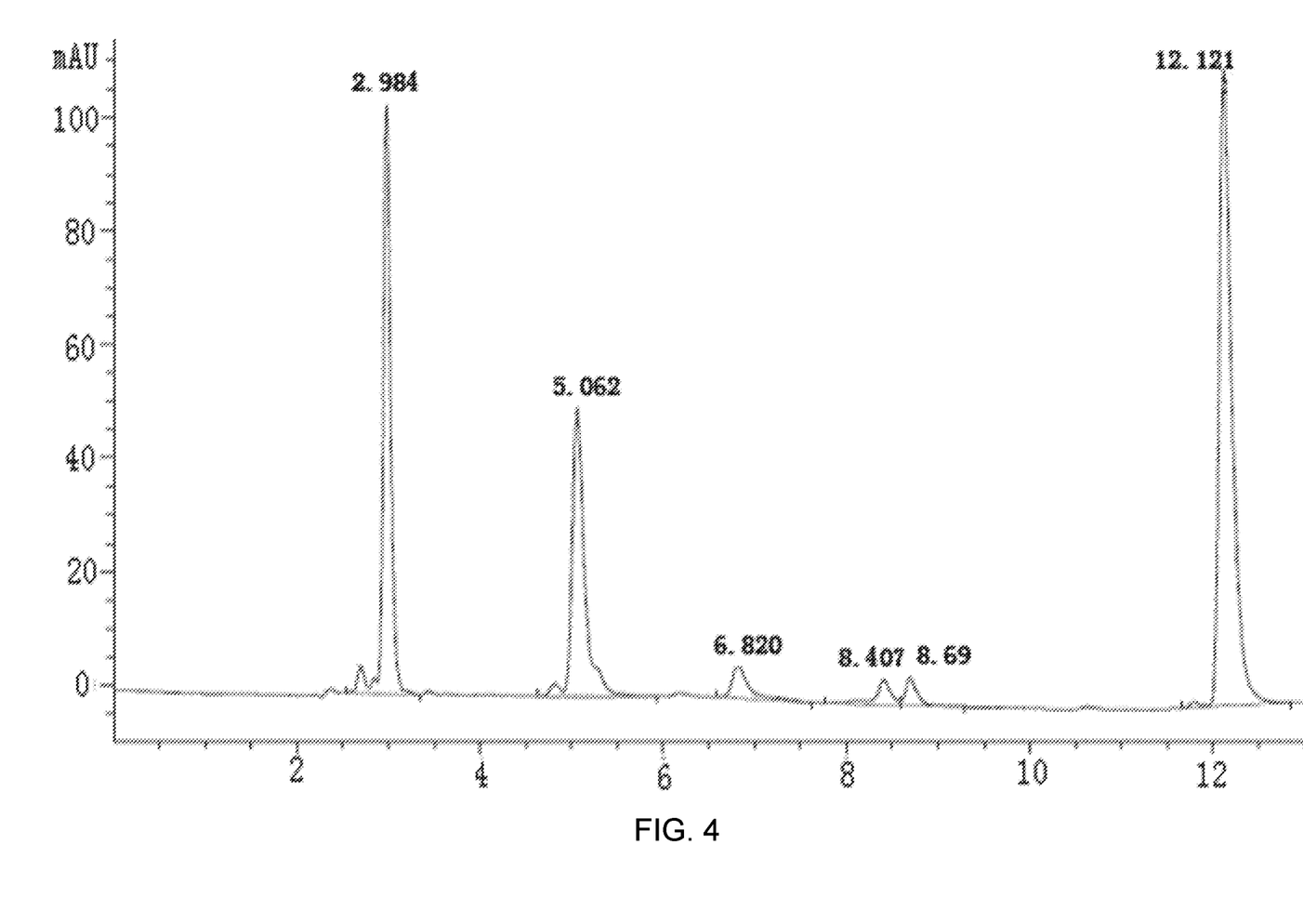
FIG. 4 is an HPLC chromatogram of an enzyme reaction solution of a mutant K115I in Embodiment 9.

A 2 L total system was designed, the final concentration of the substrate was set to 100 g/L, a clean 3 L three-necked bottle was prepared, 1 L of ddH₂O was added, then 30 g of KCl and 80 g of anhydrous $MgCl_2$ were added to be stirred and dissolved, after the solution temperature drops to room temperature, 20 g of konjac glucomannan was added, then 200 g of NMN was added and the pH was adjusted to 6 to 7 with 5 M NaOH so that the dissolution was complete. The reaction temperature was set to 37° C., 900 ml of the pure enzyme solution of the acid phosphatase mutant K115I obtained in Embodiment 5 was added, and a sodium phosphate buffer of pH 7.0 was used to be supplemented to the 2 system, and the reaction system was adjusted to pH 7.2 to start reaction. After reacting for 2 L hours, a reaction solution was taken and diluted by 50 to 100 times with pure water, and the results of the reaction were analyzed by high performance liquid chromatography after millipore filtration. The analysis method is shown in Table 3, and the HPLC chromatogram is shown in FIG. 4. The detection results show that the substrate NMN is not degraded obviously, and the conversion rate of NMN to NR is 72.5%.

Embodiment 10

After a catalytic reaction for preparing nicotinamide ribose was completed, an enzyme reaction solution was filtered through 200-400 mesh filter cloth to remove the acid phosphatase therein, 2 L to 6 M hydrochloric acid was added to an obtained filtrate to adjust the pH to about 5.0, then microfiltration was performed by a 0.45 μm microfiltration membrane, and a microfiltrate was collected; the microfiltrate was purified by a preparative liquid phase, the control conditions of the preparative liquid phase being shown in Table 4, and an eluate of an NR segment was collected to obtain a nicotinamide riboside aqueous solution having a purity greater than 99%; then, the obtained nicotinamide riboside aqueous solution having the purity greater than 99% is subjected to nanofiltration concentration at a temperature of 25° C. or below to increase the nicotinamide riboside concentration to 50 to 60 g/L, and then the hydrochloric acid was added to adjust the pH to 3 to 4; the nicotinamide riboside aqueous solution having a concentration of 90 g/L was added with the konjac glucomannan, and fully dissolved, stirred and mixed uniformly; and drying treatment was performed in a lyophilizer, the sublimation temperature in the drying process was controlled to 25° C. or below, and a white powdered nicotinamide riboside refined product could be obtained after 24 hours, and has a purity of 99% or more. The yield and purity of the nicotinamide riboside refined product obtained after separating and purifying the enzyme reaction solutions in the above-mentioned Embodiments 7, 8, and 9 are shown in Table 5.

TABLE 4

| Preparation column | Polystyrene preparation column |
| --- | --- |
| Mobile phase A: | Absolute ethanol |
| Mobile phase B: | Pure water |
| Instrument Model | Beijing Chuangxin Tongheng LC6000 |
| Detector | UV260 nm |
| Flow rate: | 40 ml/min |
| Column temperature: | 25° C. |
| Injection volume: | NR10 g (volume: not more than 200 mL) |
| Sample treatment | Microfiltration membrane |

| Gradient: | Time/min | Phase A(%) | Phase B(%) |
| --- | --- | --- | --- |
| | 0 | 0 | 100 |
| | 13 | 1 | 99 |
| | 23 | 5 | 95 |
| | 31 | 20 | 80 |
| | 43 | 20 | 80 |
| | 45 | 0 | 100 |
| | 60 | 0 | 100 |
| Remarks: | Calculated by volume ratio | | |

TABLE 5

| | Embodiment7 | Embodiment8 | Embodiment9 |
| --- | --- | --- | --- |
| Weight of lyophilized powder | 226.05 g | 389.78 g | 282.59 g |
| Purity of lyophilized powder | 99.31% | 99.70% | 99.62% |

What is claimed is:

1. A method for preparing nicotinamide riboside, wherein the method comprises: catalyzing nicotinamide mononucleotide in the presence of an acid phosphatase, KCl and anhydrous $MgCl_2$ to convert nicotinamide mononucleotide into nicotinamide riboside, wherein the acid phosphatase comprises the amino acid sequence of SEQ ID NO: 2 or comprises an acid phosphatase mutant, wherein the acid phosphatase mutant is selected from (a), (b), or (c):
   (a) an acid phosphatase mutant comprising the amino acid sequence of SEQ ID NO: 3;
   (b) an acid phosphatase mutant comprising the amino acid sequence of SEQ ID NO: 2 with the exception of a mutation or mutations selected from the group consisting of D206I, K115I, K115F, S240E, K44C, K115I/S240E, K115F/K44C/D206I, and K115I/S240E/D206I; or
   (c) an acid phosphatase mutant having a catalytic activity higher than a catalytic activity of the acid phosphatase of the amino acid sequence of SEQ ID NO: 2, wherein the acid phosphatase mutant defined by (c) has 90% or more sequence homology with the amino acid sequence of the acid phosphatase mutant defined by (a) or (b), and wherein the acid phosphatase mutant defined by (c) uses nicotinamide mononucleotide as a substrate.

2. The method for preparing nicotinamide riboside of claim 1, wherein the method sequentially comprises the following steps:
   1) dissolving KCl and anhydrous $MgCl_2$ in water to obtain a mixed solution of KCl and $MgCl_2$;
   2) cooling the mixed solution of KCl and $MgCl_2$ to room temperature;
   3) adding the nicotinamide mononucleotide to the mixed solution of KCl and $MgCl_2$, dissolving and adjusting a pH value to 6 to 7;
   4) adding the acid phosphatase to the mixed solution of KCl and $MgCl_2$ and adjusting the pH value to 6.8 to 7.3; and
   5) reacting at a temperature of 37±5° C. for at least 1.5 hours to produce the nicotinamide riboside.

3. The method for preparing the nicotinamide riboside of claim 1, wherein the method further comprises:
   adding konjac glucomannan and/or rebaudioside A to a reaction system prior to the start of the acid phosphatase catalyzing the nicotinaminde mononucleotide into the nicotinamide riboside.

4. The method for preparing the nicotinamide riboside of claim 1, the method further comprising immobilizing the acid phosphatase by adding 0.2 to 0.8 M $K_2HPO_4$ to the acid phosphatase, adjusting the pH value to 7.5 to 9.5, adding a solid phase resin to a stir at room temperature for 12 to 24 h, and then filtering to remove a filtrate to obtain the immobilized acid phosphatase.

5. The method for preparing the nicotinamide riboside of claim 1, the method further comprises a post-treatment process for obtaining a nicotinamide riboside refined product by purifying an enzyme reaction solution in which the nicotinaminde mononucleotide is catalyzed by the acid phosphatase to convert into the nicotinamide riboside, and the post-treatment process comprises the following steps:
   1) filtering the enzyme reaction solution to collect a filtrate;
   2) adjusting the pH value of the filtrate to 5.0±0.5;

3) microfiltering the filtrate of which the pH value is adjusted in step 2) to collect a filtrate;
4) purifying a microfiltrate obtained by microfiltering in step 3) with a preparative liquid phase, the preparative liquid phase using polystyrene as a filler of a preparation column, using ethanol and water as a mobile phase, performing gradient elution, and collecting an eluate of a peak of interest; and
5) lyophilizing the eluate collected in step 4) to obtain the nicotinamide riboside refined product.

* * * * *

```
SEQUENCE LISTING

<160> NUMBER OF SEQ ID NOS: 13

<210> SEQ ID NO 1
<211> LENGTH: 966
<212> TYPE: DNA
<213> ORGANISM: Saccharomyces cerevisiae

<400> SEQUENCE: 1
atgaccattg cgaaggatta ccgtaccatc tatcgtaacc agattaagaa acaaatccgt      60
ctgaaccagg agcacctgca aagcctgacc cacctgggta gccagattaa ctttgaagtg     120
gacccgccga agctgccgga tccggacccg gcgcgtaaag tttctttttt cgatatcgac     180 aacacctgt accgtaagag caccaaagtg cagctgctga tgcagcaaag cctgagcaac     240
tttttcaagt atgagctggg ctttgacgat gacgaggcgg aacgtctgat cgagagctac     300
tatcaagaat acggtctgag cgtgaaaggc ctgattaaga caaacagat cgatgacgtt     360 ctgcaataca acaccttcat tgatgacagc ctgccgctgc aagattatct gaagccggac     420
tggaaactgc gtgaactgct gatcaacctg aagaaaaaga aactgggcaa gtttgacaaa     480
ctgtggctgt tcaccaacag ctataagaac cacgcgattc gttgcgtgaa aatcctgggt     540
attgcggacc tgttcgacgg catcacctac tgccactatg atcgtccgat tgaggaagag     600
ttcatctgca agccggaccc gaaattttc gagaccgcga agctgcagag cggcctgagc     660
```

```
agctttgcga acgcgtggtt cattgatgac aacgagagca acgtgcgtag cgcgctgagc    720
atgggtatgg gccacgttat ccacctgatt gaagattacc aatatgagag cgaaaacatt    780
gttaccaagg accacaagaa caaacagcaa ttcagcatcc tgaaagatat cctggagatt    840
ccgctgatca tggacgtgga agtttaccgt ccgagcagca tcgcgattaa agagatggaa    900
gagctggaag aggaaggtga agcggtgaac tggagcaacc agcaaatcaa cgttcagagc    960
agctaa                                                                966
```

<210> SEQ ID NO 2
<211> LENGTH: 321
<212> TYPE: PRT
<213> ORGANISM: Saccharomyces cerevisiae

<400> SEQUENCE: 2

```
Met Thr Ile Ala Lys Asp Tyr Arg Thr Ile Tyr Arg Asn Gln Ile Lys
1               5                   10                  15

Lys Gln Ile Arg Leu Asn Gln Glu His Leu Gln Ser Leu Thr His Leu
            20                  25                  30

Gly Ser Gln Ile Asn Phe Glu Val Asp Pro Pro Lys Leu Pro Asp Pro
        35                  40                  45

Asp Pro Ala Arg Lys Val Phe Phe Asp Ile Asp Asn Thr Leu Tyr
    50                  55                  60

Arg Lys Ser Thr Lys Val Gln Leu Leu Met Gln Gln Ser Leu Ser Asn
65                  70                  75                  80

Phe Phe Lys Tyr Glu Leu Gly Phe Asp Asp Glu Ala Glu Arg Leu
                85                  90                  95

Ile Glu Ser Tyr Tyr Gln Glu Tyr Gly Leu Ser Val Lys Gly Leu Ile
            100                 105                 110

Lys Asn Lys Gln Ile Asp Asp Val Leu Gln Tyr Asn Thr Phe Ile Asp
        115                 120                 125

Asp Ser Leu Pro Leu Gln Asp Tyr Leu Lys Pro Asp Trp Lys Leu Arg
    130                 135                 140

Glu Leu Leu Ile Asn Leu Lys Lys Lys Leu Gly Lys Phe Asp Lys
145                 150                 155                 160

Leu Trp Leu Phe Thr Asn Ser Tyr Lys Asn His Ala Ile Arg Cys Val
                165                 170                 175

Lys Ile Leu Gly Ile Ala Asp Leu Phe Asp Gly Ile Thr Tyr Cys His
            180                 185                 190

Tyr Asp Arg Pro Ile Glu Glu Glu Phe Ile Cys Lys Pro Asp Pro Lys
        195                 200                 205

Phe Phe Glu Thr Ala Lys Leu Gln Ser Gly Leu Ser Ser Phe Ala Asn
    210                 215                 220

Ala Trp Phe Ile Asp Asp Asn Glu Ser Asn Val Arg Ser Ala Leu Ser
225                 230                 235                 240

Met Gly Met Gly His Val Ile His Leu Ile Glu Asp Tyr Gln Tyr Glu
                245                 250                 255

Ser Glu Asn Ile Val Thr Lys Asp His Lys Asn Lys Gln Gln Phe Ser
            260                 265                 270

Ile Leu Lys Asp Ile Leu Glu Ile Pro Leu Ile Met Asp Val Glu Val
        275                 280                 285

Tyr Arg Pro Ser Ser Ile Ala Ile Lys Glu Met Glu Glu Leu Glu Glu
    290                 295                 300

Glu Gly Glu Ala Val Asn Trp Ser Asn Gln Gln Ile Asn Val Gln Ser
```

Ser

<210> SEQ ID NO 3
<211> LENGTH: 321
<212> TYPE: PRT
<213> ORGANISM: Artificial sequence
<220> FEATURE:
<223> OTHER INFORMATION: The lysine was mutated to isoleucine at site 115

<400> SEQUENCE: 3

```
Met Thr Ile Ala Lys Asp Tyr Arg Thr Ile Tyr Arg Asn Gln Ile Lys
1               5                   10                  15

Lys Gln Ile Arg Leu Asn Gln Glu His Leu Gln Ser Leu Thr His Leu
            20                  25                  30

Gly Ser Gln Ile Asn Phe Glu Val Asp Pro Lys Leu Pro Asp Pro
        35                  40                  45

Asp Pro Ala Arg Lys Val Phe Phe Asp Ile Asp Asn Thr Leu Tyr
    50                  55                  60

Arg Lys Ser Thr Lys Val Gln Leu Leu Met Gln Gln Ser Leu Ser Asn
65                  70                  75                  80

Phe Phe Lys Tyr Glu Leu Gly Phe Asp Asp Glu Ala Glu Arg Leu
                85                  90                  95

Ile Glu Ser Tyr Tyr Gln Glu Tyr Gly Leu Ser Val Lys Gly Leu Ile
            100                 105                 110

Lys Asn Ile Gln Ile Asp Asp Val Leu Gln Tyr Asn Thr Phe Ile Asp
            115                 120                 125

Asp Ser Leu Pro Leu Gln Asp Tyr Leu Lys Pro Asp Trp Lys Leu Arg
    130                 135                 140

Glu Leu Leu Ile Asn Leu Lys Lys Lys Leu Gly Lys Phe Asp Lys
145                 150                 155                 160

Leu Trp Leu Phe Thr Asn Ser Tyr Lys Asn His Ala Ile Arg Cys Val
                165                 170                 175

Lys Ile Leu Gly Ile Ala Asp Leu Phe Asp Gly Ile Thr Tyr Cys His
            180                 185                 190

Tyr Asp Arg Pro Ile Glu Glu Glu Phe Ile Cys Lys Pro Asp Pro Lys
        195                 200                 205

Phe Phe Glu Thr Ala Lys Leu Gln Ser Gly Leu Ser Ser Phe Ala Asn
    210                 215                 220

Ala Trp Phe Ile Asp Asp Asn Glu Ser Asn Val Arg Ser Ala Leu Ser
225                 230                 235                 240

Met Gly Met Gly His Val Ile His Leu Ile Glu Asp Tyr Gln Tyr Glu
                245                 250                 255

Ser Glu Asn Ile Val Thr Lys Asp His Lys Asn Lys Gln Gln Phe Ser
            260                 265                 270

Ile Leu Lys Asp Ile Leu Glu Ile Pro Leu Ile Met Asp Val Glu Val
        275                 280                 285

Tyr Arg Pro Ser Ser Ile Ala Ile Lys Glu Met Glu Glu Leu Glu Glu
    290                 295                 300

Glu Gly Glu Ala Val Asn Trp Ser Asn Gln Gln Ile Asn Val Gln Ser
305                 310                 315                 320

Ser
```

<210> SEQ ID NO 4

```
<211> LENGTH: 33
<212> TYPE: DNA
<213> ORGANISM: Artificial sequence
<220> FEATURE:
<223> OTHER INFORMATION: the sequence is synthetized

<400> SEQUENCE: 4
ttcatctgca agccgattcc gaattttttc gag                              33

<210> SEQ ID NO 5
<211> LENGTH: 33
<212> TYPE: DNA
<213> ORGANISM: Artificial sequence
<220> FEATURE:
<223> OTHER INFORMATION: the sequence is synthetized

<400> SEQUENCE: 5
ctcgaaaaat ttcggaatcg gcttgcagat gaa                              33

<210> SEQ ID NO 6
<211> LENGTH: 33
<212> TYPE: DNA
<213> ORGANISM: Artificial sequence
<220> FEATURE:
<223> OTHER INFORMATION: the sequence is synthetized

<400> SEQUENCE: 6
ggcctgatta agaacattca gatcgatgac gtt                              33

<210> SEQ ID NO 7
<211> LENGTH: 33
<212> TYPE: DNA
<213> ORGANISM: Artificial sequence
<220> FEATURE:
<223> OTHER INFORMATION: the sequence is synthetized

<400> SEQUENCE: 7
aacgtcatcg atctgaatgt tcttaatcag gcc                              33

<210> SEQ ID NO 8
<211> LENGTH: 33
<212> TYPE: DNA
<213> ORGANISM: Artificial sequence
<220> FEATURE:
<223> OTHER INFORMATION: the sequence is synthetized

<400> SEQUENCE: 8
ggcctgatta agaacttcca gatcgatgac gtt                              33

<210> SEQ ID NO 9
<211> LENGTH: 33
<212> TYPE: DNA
<213> ORGANISM: Artificial sequence
<220> FEATURE:
<223> OTHER INFORMATION: the sequence is synthetized

<400> SEQUENCE: 9
aacgtcatcg atctggaagt tcttaatcag gcc                              33

<210> SEQ ID NO 10
<211> LENGTH: 33
<212> TYPE: DNA
<213> ORGANISM: Artificial sequence
<220> FEATURE:
<223> OTHER INFORMATION: the sequence is synthetized

<400> SEQUENCE: 10
```

```
gtgcgtagcg cgctggaaat gggtatgggc cac                             33

<210> SEQ ID NO 11
<211> LENGTH: 33
<212> TYPE: DNA
<213> ORGANISM: Artificial sequence
<220> FEATURE:
<223> OTHER INFORMATION: the sequence is synthetized

<400> SEQUENCE: 11
gtggcccata cccatttcca gcgcgctacg cac                             33

<210> SEQ ID NO 12
<211> LENGTH: 33
<212> TYPE: DNA
<213> ORGANISM: Artificial sequence
<220> FEATURE:
<223> OTHER INFORMATION: the sequence is synthetized

<400> SEQUENCE: 12
gaagtggacc cgccgtgcct gccggatccg gac                             33

<210> SEQ ID NO 13
<211> LENGTH: 33
<212> TYPE: DNA
<213> ORGANISM: Artificial sequence
<220> FEATURE:
<223> OTHER INFORMATION: the sequence is synthetized

<400> SEQUENCE: 13
gtccggatcc ggcaggcacg gcgggtccac ttc                             33
```